United States Patent [19]

Tsuji

[11] Patent Number: 5,060,173
[45] Date of Patent: * Oct. 22, 1991

[54] METHOD AND APPARATUS FOR DETECTING DEFECTS IN PNEUMATIC TIRE

[75] Inventor: Naotaka Tsuji, Higashiyamato, Japan

[73] Assignee: Bridgestone Corporation, Tokyo, Japan

[*] Notice: The portion of the term of this patent subsequent to Jun. 19, 2007 has been disclaimed.

[21] Appl. No.: 517,790

[22] Filed: May 2, 1990

[30] Foreign Application Priority Data

May 10, 1989 [JP] Japan .................................. 1-114969

[51] Int. Cl.$^5$ .......................................... G01M 17/02
[52] U.S. Cl. ................................ 364/551.01; 364/554; 364/560; 73/146
[58] Field of Search ................... 364/550, 551.01, 552, 364/554, 575, 560, 507, 505, 506; 73/146, 862.38, 862.45; 33/203.11

[56] References Cited

U.S. PATENT DOCUMENTS

| 3,805,036 | 4/1974 | Michaud et al. | 364/550 |
|---|---|---|---|
| 4,275,589 | 6/1981 | Dugger et al. | 73/146 |
| 4,402,218 | 9/1983 | Engel | 73/146 |
| 4,736,208 | 4/1988 | Schmidt | 364/560 |
| 4,805,125 | 2/1989 | Beebe | 73/146 |
| 4,934,184 | 6/1990 | Tsuji | 73/146 |

FOREIGN PATENT DOCUMENTS 62-298744 12/1987 Japan .

Primary Examiner—Parshotam S. Lall
Assistant Examiner—Michael Zanelli
Attorney, Agent, or Firm—Sughrue, Mion, Zinn Macpeak & Seas

[57] ABSTRACT

Internal defects formed within a substrate tire for manufacturing a retreaded tire are detected in a non-destructive manner by rotating the inflated tire at a constant speed of 1 r.p.m. while a displacement sensor is urged against an outer surface of the tire at different pressures to derive first and second sets of displacement signals, deriving displacement differences between the first and second displacement signals at corresponding measuring points on the outer surface of the tire, deriving a minimum value of the displacement differences, calculating deviations between the displacement differences and the minimum value, deriving the maximum deviation, and by comparing the maximum deviation with a first threshold value. When the maximum deviation exceeds the first threshold value, it can be judged that the tire includes a local separation. Further an average of the displacement differences is derived and is compared with a second threshold value. When the average of the displacement differences exceeds the second threshold value, it is judged that the tire includes a circumferential separation or fatigue. Moreover, a standard deviation of the displacement differences is calculated and is compared with a third threshold value. When the standard deviation exceeds the third threshold value, it is judged that the tire has the circumferential separation or fatigue.

23 Claims, 3 Drawing Sheets

FIG._2B
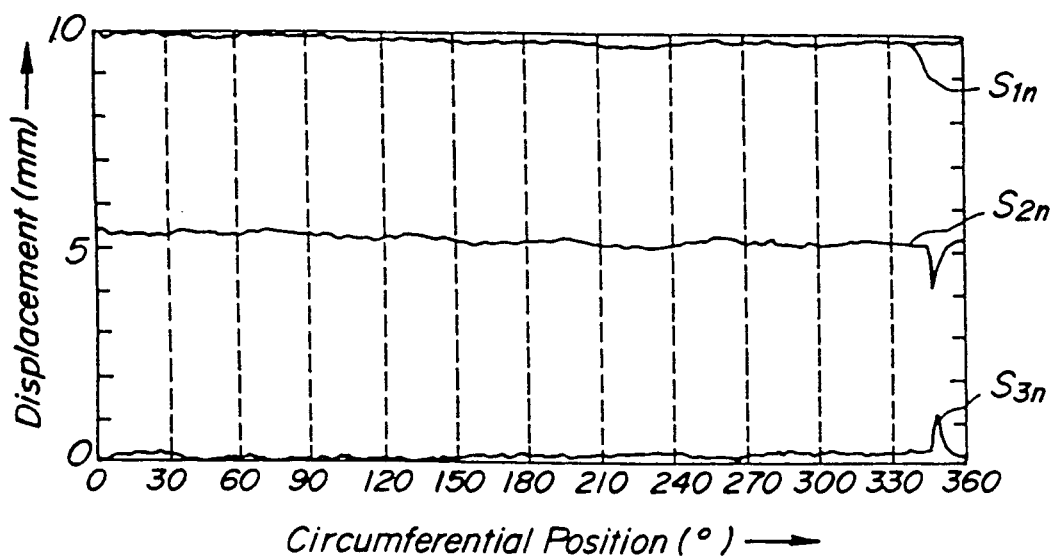
FIG._2C
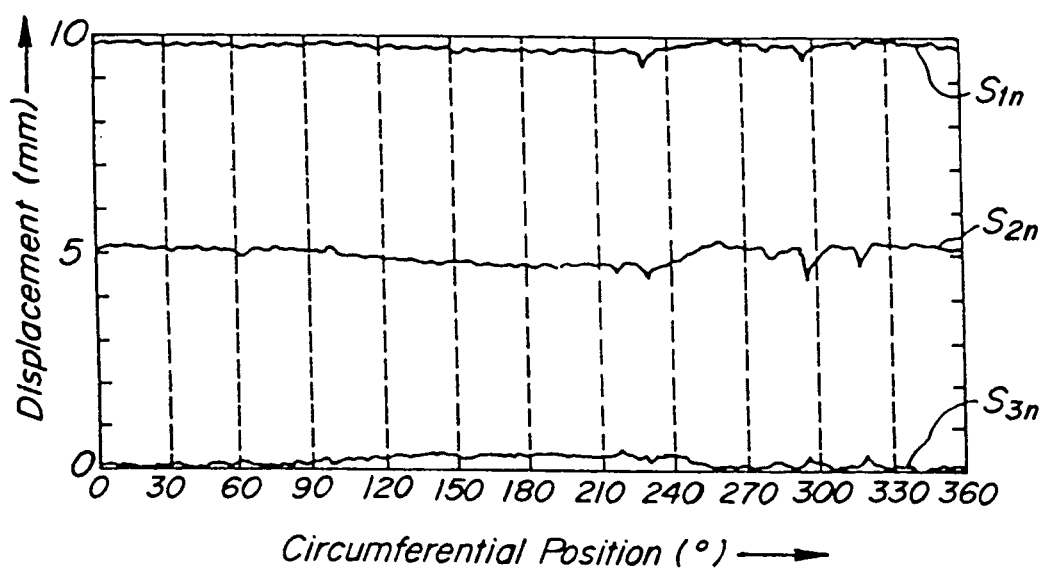

METHOD AND APPARATUS FOR DETECTING DEFECTS IN PNEUMATIC TIRE

BACKGROUND OF THE INVENTION

FIELD OF THE INVENTION AND RELATED ART STATEMENT

The present invention relates to a method and an apparatus for detecting defects formed within a tire, and more particularly to a method and an apparatus for detecting internal defects formed within a pneumatic tire in a non-destructive manner.

Heretofore, there has been developed a technique for retreading or reforming a tire from a used tire. In case of manufacturing a retreaded tire, a used tire is first buffed to remove a worn tread and to form a substrate tire having a smooth outer surface and then a new tread is applied on the smooth outer surface. In order to obtain a retreaded tire having a good quality, the quality of the substrate tire is very important. For instance, if the substrate tire includes a defect such as a local separation, a circumferential separation and fatigue which are produced in the circumferential direction over 360 degrees, it is not possible to obtain a retreaded tire having a sufficiently high quality. Therefore, it has been earnestly required to develop a method of detecting the defect formed in the substrate tire for manufacturing the retreaded tire.

In Japanese Patent Application Laid-open Publication Kokai Sho 62-298744, there has been proposed a known method of detecting the defects in the tire. In this known method, a substrate tire for forming a retreaded tire is supported by means of two rollers and two pushers are urged against an inner surface of the tire at different forces While the pushers are relatively moved in the circumferential direction of the tire to measure a difference in distortion or tension between the two pushers. Then the internal defect can be detected on the basis of the thus detected difference in distortion or tension.

In the known method just explained above, the pushers are urged against the inner wall of the tire, so that the difference in tension could not be detected accurately. That is to say, a number of reinforcing members are arranged near the inner surface of the tire, and therefore even if a separation is produced between these members, it is difficult to detect the tension difference at a high sensitivity. Further, the precision of the detection is very low. Moreover, in the substrate tire for manufacturing the retreaded tire, the separation is mainly produced at a third belt end on the outer side, but the known method is not effective for measuring such a defect.

Moreover, in the known method the pushers are moved relatively to the tire placed on the two rollers and the difference in distortion is detected. Therefore, the entire detecting apparatus is liable to be large in size. Further, it is rather difficult to hold the substrate tire stably on the two rollers, so that the operation becomes cumbersome and a large noise might be produced.

In the known method the difference in distortion between two points is detected, so that only the local separation can be detected and it is impossible to detect the circumferential separation generated along the entire circumference of the tire and the fatigue which has not been grown into the separation.

SUMMARY OF THE INVENTION

The present invention has for its object to provide a novel and useful method and apparatus for detecting any kinds of defects such as the local separation, circumferential separation and fatigue in pneumatic tires accurately at a high sensitivity and in a simple manner.

According to the invention, a method of detecting defects formed within pneumatic tires in a non-destructive manner comprises the steps of:

rotating a pneumatic tire inflated with a predetermined internal pressure;

urging at least one displacement sensor against an outer surface of an inflated pneumatic tire;

deriving from said displacement sensor a first set of displacement signals $S_{1n}$ which represent displacements of the outer surface of tire at n measuring points on the outer surface of the tire along a circumference thereof when the displacement sensor is urged against the tire at a first pressure and a second set of displacement signals $S_{2n}$ which represent displacements of the outer surface of tire at said n measuring points when the displacement sensor is urged against the outer surface of the tire at a second pressure which is different from said first pressure;

deriving displacement differences $\Delta S_n$ at the n measuring points on the tire from said first and second sets of displacement signals; and detecting a defect or defects formed within the tire on the basis of said displacement differences.

Since the pneumatic tire has an elasticity, when the displacement sensor is urged against the outer surface of the tire, the elastic repelling force is applied to the displacement sensor. In this case, the elastic repelling force produced at a portion of the tire at which an internal defect such as the local separation is formed is generally smaller than that produced at a portion where the separation is not formed. Therefore, when the displacement sensor is pushed onto the outer surface of the tire at a pressure which is larger than a given value, the displacement sensor detects a relatively large displacement. To the contrary, when the displacement sensor is urged against the outer surface of the tire at a low pressure such that the outer surface of the tire is not substantially deformed, it is possible to derive displacement information which represents the contour configuration of the outer surface of the tire. Therefore, according to the invention, a first set of displacement signals $S_{1n}$ at respective measuring points along the whole circumference of the outer surface of the tire is derived at a low pressure at which the outer surface of the tire is not substantially deformed, next a second set of displacement signals $S_{2n}$ at the same measuring points is derived at a high pressure at which the outer surface of the tire is elastically deformed, and after that displacement differences $\Delta S_n (=S_{2n}-S_{1n})$ are calculated. Then the displacement differences $\Delta S_n$ represents information about the internal defects formed within the tire. It should be noted that a displacement difference $\Delta S$ is small at a point where no defect is formed, while a displacement difference $\Delta S$ is larger at a point at which a defect is produced. Therefore, in a preferable embodiment of the method according to the invention, the minimum displacement difference $\Delta S_{min}$ is first derived among all the displacement differences and then deviations $S_{1n}$ are derived on the basis of the detected minimum displacement difference $\Delta S_{min}$. When the deviation exceeds a first threshold having a predetermined value, it can be judged that a local defect is produced. When the circumferential separation or fatigue is produced over the entire circumference of the tire, the displacement differences $\Delta S_n$ become generally larger and the peak of the deviation becomes smaller. Therefore, the peak-peak value of the deviation curve cannot be effectively utilized to detect the defect. In such a case, according to the invention, an average value of the deviation is calculated and when the thus calculated average value exceeds a second threshold having a predetermined value, it is judged that there is an internal defect. Further when circumferential separation or fatigue is produced in the tire, the displacement differences $\Delta S_n$ fluctuate largely. In another preferable embodiment of the method according to the invention, the fluctuation of the displacement differences $\Delta S_n$, i.e. a distribution of the displacement differences in the circumferential direction is derived. The fluctuation may be formed by, for instance, the standard deviation or the dispersion.

BRIEF DESCRIPTION OF THE DRAWINGS

FIGS. 2A, 2B and 2C are graphs illustrating actual measuring results obtained by the apparatus shown in FIG. 1;

DESCRIPTION OF THE PREFERRED EMBODIMENT

Figure 1:
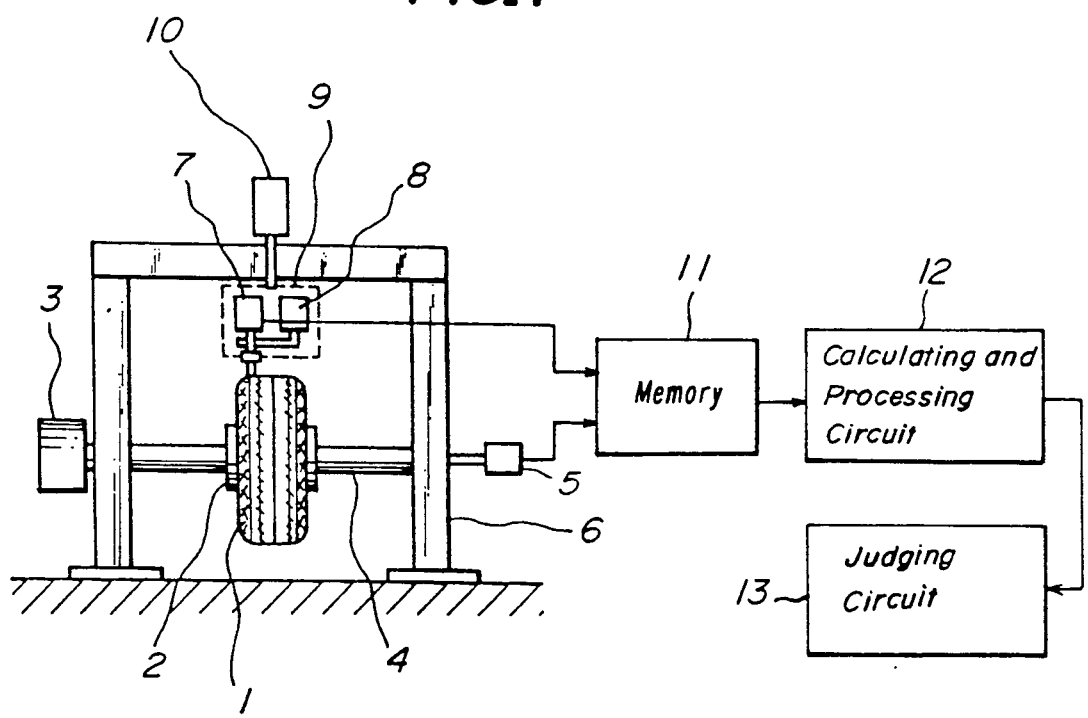
FIG. 1 is a schematic view showing an internal defect detecting apparatus according to the invention for carrying out an embodiment of the method according to the invention.

FIG. 1 is a schematic view showing a first embodiment of the defect detecting apparatus according to the invention. A pneumatic tire 1 whose defect or defects are to be detected is set on a half limb 2 and the half limb is coupled with an output shaft 4 of a motor 3. To the free end of shaft 4 is secured a rotary encoder 5 which detects the positional information in the circumferential direction of the tire. The motor 3 and rotary encoder 5 are supported by a supporting frame 6. The tire 1 is inflated to such an inner pressure that the tire can be self-sustained. This inner pressure may be about 0.5 kg/cm² to 2.0 kg/cm². Above the tire 1 are arranged a displacement sensor 7 and a pressure cylinder 8 for urging the displacement sensor against the outer surface of the tire at a given pressure. The displacement sensor 7 and cylinder 8 are mounted on a supporting member 9 which is coupled with a position adjusting member 10. The position adjusting member 10 is secured to the supporting frame 6. The position adjusting member 10 serves to move the supporting member 9 up and down as well as in an axial direction of the tire 1. The tire 1 is rotated at a given speed such as 1 r.p.m. and the positional information of the tire 1 detected by the rotary encoder 5 is supplied to a memory 11 and is stored therein. While the tire 1 is rotated, a roller provided at a tip of the displacement sensor 7 is urged against the outer surface of tire to detect a distance between the center axis of the tire to the outer surface. That is to say, the displacement of the outer surface of tire 1 is detected. The detected displacement is also stored in the memory 11. In the memory 11 the displacement of the outer surface of tire is stored in relation to the positional information supplied from the rotary encoder 5. In the present embodiment, the displacement signal is sampled at 600 points which are equidistantly distributed along the circumference of the outer surface of tire, so that every time the tire 1 is rotated by an angle of 360/600 degrees, the displacement signal supplied from the displacement sensor 7 is sampled and a sampled signal is stored in the memory 11. The number of sampling points may be set to a value within a range of 300~2,000.

Now the operation for detecting the internal defects in the tire will be explained. First, the pressure at which the displacement sensor 7 is urged against the outer surface of tire is adjusted to 0.3 to 0.5 kg/cm² by means of the position adjusting device 10. It should be noted that the above mentioned pressure range is selected such that the tire 1 is not substantially deformed by the roller provided rotatably at a free end of the displacement sensor 7. Then the tire 1 is rotated at the constant speed of 1 r.p.m. and the displacement signal supplied from the displacement sensor 7 is sampled and stored in the memory 11 over one revolution of the tire. It should be noted that the tire 1 may be rotated at a speed within a range of 0.5~5 r.p.m. In this manner, a first set of displacement signals $S_{1n}$ (n=1, 2 ... 600) is stored in the memory 11. Then the cylinder 8 is driven to urge the roller of the displacement sensor 7 against the outer surface of tire at 20 kg which is higher than that of the first measurement. This higher pressure may be set to a value within a range of 3 to 25 kg. After the rotary encoder 5 is reset, a second set of displacement signals $S_{2n}$ is detected and are stored in the memory 11. The pressure in the seoond measurement is set to such a value that if the tire has internal defects such as separation and fatigue, the tire is deformed by the displacement sensor.

The first and second sets of the displacement signals $S_{1n}$ and $S_{2n}$ stored in the memory 11 in the manner explained above are supplied to a calculating and processing circuit 12 to derive differences in displacement at all the sampling positions along one revolution of the tire 1.

$$\Delta S_n = |S_{1n} - S_{2n}| \qquad (1)$$

It should be noted that the displacement difference $\Delta S_n$ becomes larger when the local separation is produced within the tire, but when the tire does not include the separation and fatigue, the value of $\Delta S_n$ becomes small. In the present embodiment, at first the minimum displacement difference $\Delta S_{min}$ is derived from 600 displacement differences $\Delta S_1$ to $\Delta S_{600}$. Then deviations $S_{3n}$ are calculated in accordance with the following equation, while the minimum displacement difference $\Delta S_{min}$ is set as a standard value.

$$S_{3n} = \Delta S_n - \Delta S_{min} \qquad (2)$$

Next the maximum value $S_P$ of the deviations is derived and is supplied to a judging circuit 13. In the judging circuit 13, the maximum deviation $S_P$ is compared with a predetermined threshold value stored in the judging circuit. When the maximum deviation $S_P$ exceeds a threshold value $S_T$, the judging circuit 13 judges that the tire has a local separation.

In the present embodiment, an average value $S_M$ of 600 displacement differences $\Delta S_n$ is calculated by the calculating circuit 12 in accordance with the following equation.

$$S_M = \frac{1}{600} \cdot \sum_{n=1}^{600} \Delta S_n \quad (3)$$

The thus calculated average value $S_M$ of the displacement differences is supplied to the judging circuit 13 and is compared with a predetermined threshold value stored in the judging circuit. When average exceeds the threshold value, it is judged that the tire includes the circumferential separation or fatigue.

Further, in the calculating circuit 12, a standard deviation $S\sigma$ is calculated in accordance with the following equation.

$$S\sigma = \sqrt{\frac{1}{600} \sum_{n=1}^{600} \left( S_{3n} - \frac{1}{600} \sum_{n=1}^{600} S_{3n} \right)^2} \quad (4)$$

The calculated standard deviation $S\sigma$ is then supplied to the judging circuit 13 and is compared with a predetermined threshold value stored therein. When the standard deviation $S\sigma$ is larger than the threshold value, it is judged that the tire 1 includes the defect or defects which distribute over a wide range in the circumferential direction of the tire. That is to say, it can be judged that the tire includes the circumferential separation or fatigue.

Figure 2A:
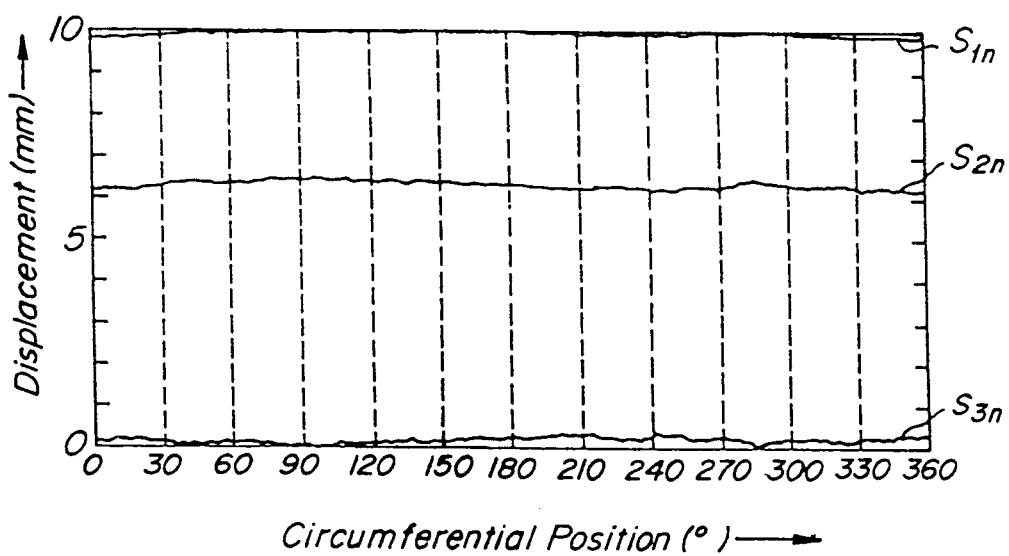

FIGS. 2A to 2C show graphs representing some examples of actual measuring results. In these graphs, the abscissae denotes the circumferential position on the outer surface and the coordinate shows the displacement in unit of mm from the reference position. FIG. 2A shows the result of a substrate tire having good quality, and the displacement differences are small over one revolution of the tire. FIG. 2B represents the measurement result of a tire having a local separation. That is to say, the displacement has a fluctuation peak at a position within a range of 330~360 degrees and it can be judged that the local separation is existent in this region. Therefore, this tire can be judged as having the internal defect and can be rejected. FIG. 2C denotes the result of a tire having the circumferential separation or fatigue. There is no peak in the displacement difference, but the values of the displacement differences $\Delta S_n$ are generally large. Further the deviation $S_{3n}$ is rather large over the whole circumference of the tire. If the judgement is effected by considering the maximum displacement difference $S_P$, this tire might be erroneously judged to be a good tire. However, according to the invention, this tire can be correctly rejected by deriving the average of the displacement differences and the distribution of the displacements. In this manner, according to the invention it is possible to detect the internal defects within the tire precisely at a high sensitivity.

Figure 3:
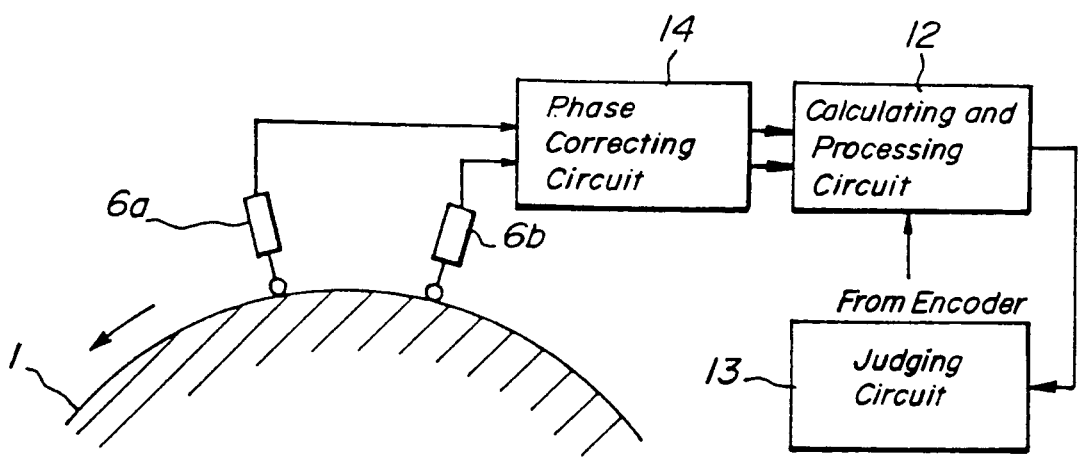
FIG. 3 is a schematic view depicting a major portion of an apparatus for performing still another embodiment of the method according to the invention.

FIG. 3 is a schematic view illustrating a major portion of another embodiment of the apparatus according to the invention. In this embodiment, portions similar to those shown in FIG. 1 are denoted by the same reference numerals used in FIG. 1.

In the present embodiment, two displacement sensors 6a and 6b are arranged such that these sensors trace the same locus on the outer surface of the tire 1, but are separated from each other by a predetermined distance. The displacement sensors 6a and 6b are urged against the outer surface of tire 1 at a substantially zero pressure and a higher pressure which may be 4~12 kg. The output signals generated by the displacement sensors 6a and 6b are supplied to the calculating and processing circuit 12 via a phase correcting circuit 14 which corrects a phase difference between the output signals. That is to say, the output signal from the displacement sensor 6a is delayed with respect to the output signal from the second displacement sensor 6b by a time period which is equal to a time during which a point on the outer surface of tire moves from the second displacement sensor 6b to the first displacement sensor 6a. Therefore, the displacement signals on the same point on the outer surface of tire 1 are simultaneously supplied to the calculating and processing circuit 12. It should be noted that the output of the rotary encoder is supplied to the calculating and processing circuit 12.

The operation of the second embodiment is substantially same as that of the first embodiment, but a necessary measuring time can be reduced to a large extent. That is to say, in the present embodiment the two displacement signals $S_{1n}$ and $S_{2n}$ can be obtained substantially simultaneously and further the change in the pressure of the displacement sensor is not required and therefore the measuring time can be reduced to a time shorter than half of that of the previous embodiment.

Figure 4:
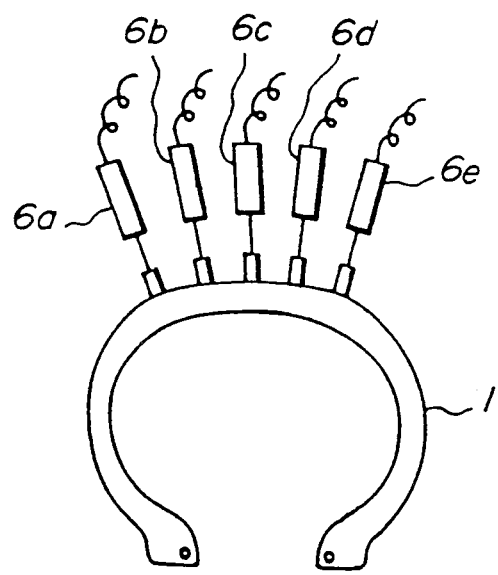
FIG. 4 is a schematic view showing a major portion of another embodiment of the defect detecting apparatus according to the invention.

The present invention is not limited to the embodiments explained above, but many alternations and modifications can be conceived by those skilled in the art within the scope of the invention. In the above embodiments, the two kinds of displacement values are detected along a single circumference on the outer surface of tire, but the measurement may be performed along a plurality of circumferences which are spaced from each other in the axial direction of the tire. In this case, a plurality of displacement sensors 6a to 6e may be aligned in the axial direction of the tire as illustrated in FIG. 4 to obtain plural kinds of displacement values simultaneously. It is also possible to arrange a single displacement sensor movably in the axial direction.

Moreover, it is also possible to detect the displacement values over one revolution of the tire while the higher pressure under which the displacement sensor is urged against the outer surface of tire is changed. Then the judgment of the tire can be effected much more precisely by comparing the two kinds of displacement values.

Further, in the above embodiments, the internal defects formed within the substrate tire for forming the retreaded tire are detected, but according to the invention it is possible to detect the defects of tires other than the substrate tire. For instance, a racing tire having a substantially smooth outer surface may be checked by the method according to the invention.

In the above explained embodiments, the displacement sensor is urged against the tread portion of tire, but the displacement sensor may be urged against the side wall of tire to detect defects formed within the side wall of tire.

As explained above in detail, the method and apparatus according to the invention can provide the following advantages.

(1) The tire is inflated to such an inner pressure that the tire can be self-sustained and the displacement is measured from the outside of the tire, while the tire is rotated, and thus the measuring operation can be performed easily and further the detecting precision can be increased.

(2) Not only the local separation, but also the circumferential separation and fatigue can be detected by deriving the displacement values at the measuring points along the circumference of the tire as well as the displacement differences, the average of the displacement differences and the distribution of the displacement differences. Therefore, the quality of the tire can be judged accurately.

(3) The displacement sensor is urged against the outer surface of tire, so that the measurement is hardly affected by the reinforcing members and the defects can be detected precisely.

What is claimed is:

1. A method of detecting internal defects formed within a pneumatic tire in a non-destructive manner comprising the steps of:

rotating an inflatable pneumatic tire inflated with a predetermined internal presusre;

uriging at least one displacement sensor against an outer surface of said inflated pneumatic tire;

deriving from siad displacement sensor a first set of displacement signals $S_{1n}$ which represent displacements of the outer surface of tire at N measuring points on the outer surface of the tire along a circumference thereof when the displacement sensor is urged against the tire at a first pressure and a second set of displacement signals $S_{2n}$ which represent displacements of the outer surface of tire at said N measuring points when the displacement sensor is urged against the outer surface of the tire at a second pressure which is different from said first pressure;

deriving displacement differences $\Delta S_n$ at the N measuring points on the tire from said first and second sets of displacement signals; and determining the presence of a defect within the tire on the basis of an analysis of said displacement differences.

2. A method according to claim 1, wherein said step of determining the defect comprises deriving the minimum displacement difference $\Delta S_{min}$ among all the displacement differences $\Delta S_n$, deriving deviations $S_{3n}$ at the N measuring points from an equation $S_{3n} = \Delta S_n - \Delta S_{min}$, deriving the maximum deviation $S_P$ among all the deviations, and comparing the maximum deviation $S_P$ with a predetermined first threshold.

3. A method according to claim 2, wherein said determining step further comprises deriving an average $S_M$ of said displacement differences $\Delta S_n$, and comparing the average $S_M$ with a second predetermined threshold value.

4. A method according to claim 2, wherein said determining step comprises deriving a standard deviation $S\sigma$ from the deviations $S_{3n}$ from an equation $$S\sigma = \sqrt{\frac{1}{N} \sum_1^N \left( S_{3n} - \frac{1}{N} \sum_1^N S_{3n} \right)^2}$$

, and comparing the standard deviation With a predetermined third threshold.

5. A method according to any one of claims 1 to 4, wherein each of said first and second sets of displacement signals are derived at 300~2,000 measuring points along the circumference of the outer surface of the inflated tire.

6. A method according to claim 5, wherein said inflated tire is rotated at a constant speed of 0.5~5 r.p.m.

7. A method according to any one of claims 1 to 4, wherein said pneumatic tire is inflated with such a pressure that the tire is self-sustained.

8. A method according to claim 7, wherein said pneumatic tire is inflated with a pressure in a range of 0.5 to 2.0 $kg/cm^2$.

9. A method according to any one of claims 1 to 4, wherein said first pressure at which said first set of displacement signals are derived is set to such a value that the outer surface of the tire is not substantially deformed, and said second pressure at which said second set of displacement signals are derived is set to such a value that the outer surface of the inflated tire is deformed.

10. A method according to claim 9, wherein said first pressure is set to a value selected from a range of 0.3 to 0.5 kg.

11. A method according to claim 9, wherein said second pressure is set to a value selected from a range of about 3 to 25 kg.

12. A method according to any one of claims 1 to 4, wherein said first and second sets of displacement signals are derived by means of a single displacement sensor by changing the pressure at which the displacement sensor is brought into contact with the outer surface of the inflated tire.

13. A method according to any one of claims 1 to 4, wherein said first and second sets of displacement signals are derived with first and second displacement sensors, respectively, which are simultaneously brought into contact with the outer surface of the inflated tire at said first and second pressures at positions which are on the same circumferential locus of the tire, but are separated from each other in the circumferential direction.

14. A method according to claim 13, wherein said first and second sets of displacement signals are derived substantially simultaneously by supplying output signals from the first and second displacement sensors through a phase correcting circuit.

15. A method according to any one of claims 1 to 4, wherein plural pairs of said first and second sets of displacements signals are derived by using plural displacement sensors which are separated from each other in an axial direction of the tire.

16. A method according to any one of claims 1 to 4, wherein plural pairs of said first and second sets of displacement signals are derived by changing the internal pressure of the inflated tire.

17. An apparatus for detecting defects formed within pneumatic tires in a non-destructive manner comprising:

a supporting means for supporting a rotatable a pneumatic tire inflated with a predetermined internal pressure;

a tire rotating means for rotating the inflated tire at a given speed;

a position detecting means for generating a position signal representing N measuring points set along a circumference of an outer surface of the tire;

a displacement detecting means for detecting displacements of an outer surface of the tire and including at least one displacement sensor and a pushing means for urging the displacement sensor against the outer surface of the tire at at least first and second pressures while the tire is rotated by said tire rotating means to derive first and second sets of displacement signals $S_{1n}$ and $S_{2n}$ at said N measuring points:

a memory means for storing said first and second sets of displacement signals $S_{1n}$ and $S_{2n}$ supplied from said displacement detecting means in conjunction with said position signal;

a calculating and processing means for calculating from the stored first and second sets of displacement signals $S_{1n}$ and $S_{2n}$ displacement differences $\Delta S_n = |S_{1n} - S_{2n}|$ at said N measuring points: and a judging means for detecting an internal defect or defects within the tire on the basis of said displacement differences $\Delta S_n$.

18. An apparatus according to claim 17, wherein said calculating and processing means is constructed such that the minimum displacement difference $\Delta S_{min}$ is derived from all the displacement differences, deviations $S_{3n} = \Delta S_n - \Delta S_{min}$ are derived, and the maximum deviation $S_p$ is derived among the deviations $S_{3n}$, and said judging means is constructed such that said maximum deviation $S_P$ is compared with a predetermined threshold value.

19. An apparatus according to claim 18, wherein said calculating and processing means is constructed to calculate an average of all the displacement differences $\Delta S_n$, and said judging means is constructed to compare the average value of the displacement differences with a predetermined threshold value.

20. An apparatus according to claim 18, wherein said calculating and processing means is constructed such that the minimum displacement difference $\Delta S_{min}$ is derived from all the displacement differences, deviations $S_{3n} = \Delta S_n - \Delta S_{min}$ are derived, and a standard deviation $S\sigma$ is calculated by an equation of $$S\sigma = \sqrt{\frac{1}{N} \sum_1^N \left( S_{3n} - \frac{1}{N} \sum_1^N S_{3n} \right)^2}$$

and said judging means is constructed to compare the standard deviation with a predetermined threshold value.

21. An apparatus according to any one of claims 17 to 20, wherein said displacement detecting means comprises a single displacement sensor, a pressure means for changing a pressure at which said displacement sensor is urged against the outer surface of the tire, and a means for changing a position of the displacement sensor in an axial direction of the tire.

22. An apparatus according to any one of claims 17 to 20, wherein said displacement detecting means comprises first and second displacement sensors which are arranged on the same circumference of the tire, but are separated from each other in the circumferential direction of the tire, and a means for urging the first and second displacement sensors against the outer surface of the tire at the first and second pressures, respectively.

23. An apparatus according to any one of claims 17 to 20, wherein said displacement detecting means comprises a plurality of displacement sensors which are brought into contact with the outer surface of the tire along a plurality of loci which are separated from each other in an axial direction of the tire.

* * * * *